US006168946B1

(12) United States Patent
Houghton et al.

(10) Patent No.: US 6,168,946 B1
(45) Date of Patent: *Jan. 2, 2001

(54) GP75 AS A TUMOR VACCINE FOR MELANOMA

(75) Inventors: Alan N. Houghton; Setaluri Vijayasaradhi, both of New York, NY (US)

(73) Assignee: Sloan-Kettering Institute for Cancer Research, New York, NY (US)

( * ) Notice: Under 35 U.S.C. 154(b), the term of this patent shall be extended for 0 days.

This patent is subject to a terminal disclaimer.

(21) Appl. No.: 08/409,794

(22) Filed: Mar. 24, 1995

Related U.S. Application Data

(63) Continuation of application No. 07/952,620, filed as application No. PCT/US91/01942 on Mar. 22, 1991, now abandoned, which is a continuation-in-part of application No. 07/497,371, filed on Mar. 22, 1990, now abandoned.

(51) Int. Cl.$^7$ .............................. C12N 15/12; C12N 1/20; C12N 5/00

(52) U.S. Cl. ................................. 435/252.33; 435/320.1; 435/325; 536/23.5

(58) Field of Search .............................. 435/69.6, 240.26, 435/240.27, 172.3, 320.1, 325, 252.33; 530/388.85; 935/15; 536/23.5

(56) References Cited

U.S. PATENT DOCUMENTS

| H819 | * | 9/1990 | Srivastava et al. .................. 530/389 |
|---|---|---|---|
| 4,414,148 | * | 11/1983 | Jansen et al. ........................ 424/85.8 |
| 4,591,572 | * | 5/1986 | Matteo et al. .................. 530/388.85 |
| 4,798,790 | * | 1/1989 | Thomson et al. ........................ 435/7 |
| 4,806,628 | * | 2/1989 | Albino et al. .................. 530/388.85 |
| 4,808,704 | * | 2/1989 | Old et al. ........................ 530/358.85 |
| 4,851,510 | * | 7/1989 | Khan .................................. 435/240 |
| 5,009,995 | * | 4/1991 | Albino et al. ........................ 435/7.23 |
| 5,059,523 | * | 10/1991 | Rettig et al. ........................ 435/7.23 |
| 5,141,742 | * | 8/1992 | Brown et al. . |
| 5,262,117 | * | 11/1993 | Brown et al. . |

FOREIGN PATENT DOCUMENTS

| 0208902 | | 11/1987 | (EP) . |
|---|---|---|---|
| 178931 | * | 1/1987 | (NO) . |
| WO9102062 | * | 2/1993 | (WO) . |

OTHER PUBLICATIONS

Tai, T. et al., (1983) Glycoproteins as Differentiation Markers in Human Malignant Melanoma and Melanocytes, *Cancer Research*, 43:2773–2779; (Exhibit C).

Vijayasaradhi, S. and Houghton, A., (1991) Purification of an Autoantigenic 75–kDa Human Melanosomal Glycoprotein, *Int. J. Cancer*, 47:298–303. (Exhibit D).

Broome, S., and Gilbert, W., (1978) "Immunological Screening Method to Detect Specific Translation Products", *Proc. Natl. Acad. Sci.*, 75:2746–49 (Exhibit D).

Kwon et al., (1991) "A Melanocyte–Specific Gene, Pmel 17, Maps Near the Silver Coat Color on Mouse Chromosome 10 and is in a Syntenic Region on Human Chromosome 12", *Proc. Natl. Acad. Sci. USA*, 88:9228–32 (Exhibit E).

Vijayasaradhi, S. et al., (1991) "Biosynthesis and Intracellular Movement of the Melanosomal Membrane Glycoprotein GP75, the Human b (Brown) Locus Product", *Experimental Cell Research*, 196:233–40 (Exhibit F).

Jackson, Ian J., (1988) "A cDNA encoding Tyrosinase–related Protein Maps to the Brown Locus in Mouse", Proceedings of the National Academy of Sciences USA, vol. 85, No. 12:4392–4396.

Burgess et al. Journal of Cell Biology 111:2129–2138, Nov. 1990.

LAzar et al. Mol. Cell. Biol. 8(3):1247–1252, Mar. 1988.

Kwon et al, Mol. Biol. & Med., 4(6):339–356 (1987) "A Melanocyte–specific cDNA clone whole expression is inducible . . . ".

Natali et al, Cancer Research, 4:583–589 (Feb. 1982) Tissue Dist., Molec. Profile & Shedding of a Cytopl. Ant. Identified by Mab.

Thomson et al, J of Invest. Derm., 90(4):459–466 (1988) "Antigenic Markers of Human Pigmented Cells".

Holzmann, et al., *J. Exp. Med.* 161(2):366–377 (1985).

Thomson T.M., *J. Investigative Dermatol.* 85(2):169–174 (1985).

* cited by examiner

Primary Examiner—Marianne P. Allen
(74) *Attorney, Agent, or Firm*—John P. White; Cooper & Dunham LLP

(57) ABSTRACT

The present invention provides an isolated nucleic acid molecule whose sequence encodes the amino acid sequence for gp75 or a fragment thereof. The present invention further provides an isolated cDNA molecule of the gp75 nucleic acid molecule or a fragment thereof and the amino acid sequence derived therefrom. This invention also provides vaccines for stimulating or enhancing in a subject to whom the vaccine is administered production of antibodies directed against gp75. This invention further provides methods using the vaccines of this invention for stimulating or enhancing production of antibodies against gp75 as well as for treating, preventing or delaying the recurrence of cancer.

8 Claims, 4 Drawing Sheets

FIGURE 2

Amino acid sequence of three peptides derived from gp75

1. Asn-Thr-Val-Glu-Gly-Tyr-Ser-Asp-Pro-Thr-Gly-Lys-Tyr-Asp-Pro-Ala-Val
2. Met-Phe-Val-Thr-Ala-Pro-Asp-Asn-Leu-Gly-Tyr-Thr-Tyr-Glu
3. Asn-Phe-Asp-Ser-Thr-Leu-Ileu-Ser-Pro-Asn-Ser-Val-Phe-Ser

FIGURE 3

Partial cDNA Sequence of gp75

5' GGACCAGCTTTTCTCACATGGCACAGGTACCACCTCCTGCGTCTGGAGAAAGA
CATGCAGGAAATGTTGCAAGAGCCTTCTTTCTCCCTTCCTTACTGGAATTTTGCAACG
GGGAAAAATGTCTGTGATATCTGCACGGATGACTTGATGGGATCCAGAAGCAACTTTG
ATTCCACTCTAATAAGCCCAAACTCTGTCTTTTCTCAATGGCGAGTGGTCTGTGACTC
CTTGGAAGATTATGATACCCTGGGAACACTTTGTAACAGCACCGAGGATGGGCCAATT
AGGAGAAATCCAGCTGGAAATGTGGCCAGACCAATGGTGCAACGTCTTCCTGAACCAC
AGGATGTCGCTCAGTGCTTGGAAGTTGGTTTATTTGACACGCCTCCTTTTTATTCCAA
CTCTACAAACAGTTTCCGAAACACAGTGGAAGGTTACAGTGACCCCACGGGAAAGTAT
GACCCTGCTGTTCGAAGTCTTCACAATTTGGCTCATCTATTCCTGAATGGAACAGGGG
GACAAACCCATTTGTCTTCCCAAGATCCTATTTTTGTCCTCCTGCACACCTTCACAGA
TGCAGTCTTTGATGAATGGCTAAGGAGATACAATGCTGATATATCCACATTTCCATTG
GAAAATGCCCCTATTGGACATAATAGACAATACAACATGGTGCCATTCTGGCCCCCAG
TCACCAACACAGAAATGTTTGTTACTGCTCCAGACAACCTGGGATACACTTATGAA 3'

Isolation of a full length cDNA encoding gp75

Partial Restriction map

Nucleootide Sequence:

```
                 EcoRI
                   ↓
      5'    TAAAACATTTC  AATTCTAAGAGAGTCATC...    3'
```

GP75 AS A TUMOR VACCINE FOR MELANOMA

This is a continuation of application Ser. No. 07/952,620, filed Nov. 23, 1992, now abandoned, which is the U.S. national stage of international application PCT/US 91/01942, filed Mar. 22, 1991, which is a continuation-in-part of U.S. Ser. No. 7/497,431, filed Mar. 22, 1990, now abandoned the contents of which are hereby incorporated by reference into the present application.

The invention disclosed herein was made with Government support under NIH Grant No. CA 08748 from the Department of Health and Human Services. Accordingly, the U.S. Government has certain rights in this invention.

Throughout this application various publications are referenced. The disclosure of these publications, in their entireties, are hereby incorporated by reference into this application in order to more fully described the state of the art to which this invention pertains.

BACKGROUND OF THE INVENTION

The molecular identification of immunogenic determinants on human cancer cells provides a basis for understanding the immune response to cancer. On human melanoma cells, two classes of antigens have received particular attention as targets for immune recognition: 1) unique antigens expressed only by autologous melanoma cells (Old, L. J. (1981), Cancer immunology: The search for specificity. G. H. A. Clowes Memorial Lecture, *Cancer Res.* 41:361; Carey, T. E., T. Takahashi, L. A. Resnick, H. F. Oettgen, and L. J. Old. (1976), Cell surface antigens of human malignant melanoma. I. Mixed hemadsorption assay for humoral immunity to cultured autologous melanoma cells, *Proc. Natl. Acad. Sci. USA*. 73:3278; Real, F. X., M. J. Mattes, A. N. Houghton, H. F. Oettgen, K. O. Lloyd, and L. J. Old. (1984), Class 1 (unique) antigens of human melanoma: Identification of a 90,000 dalton cell surface glycoprotein by autologous antibody, *J. Exp. Med* 160:1219) and 2) differentiation antigens normally expressed by cells of the melanocytic lineage (Houghton, A. N., M. C. Taormina, H. Ikeda, T. Watanabe, H. F. Oettgen, and L. J. Old. (1980), Serological survey of normal humans for natural antibody to cell surface antigens of melanoma, *Proc. Natl. Acad. Sci. USA*. 77:4260; Houghton, A. N., M. Eisinger, A. P. Albino, J. G. Cairncross, and L. J. Old. (1982), Surface antigens of melanocytes and melanoma: Markers of melanocyte differentiation and melanoma subsets, *J. Exp. Med.* 156:1755; Houghton, A. N., F. X. Real, L. J. Davis, C. Cardon-Cardo, and L. J. Old. (1987), Phenotypic heterogeneity of melanoma: Relation to the differentiation program of melanoma cells, *J. Exp. Med.* 164:812). Differentiation antigens of melanocytes have been defined by their relationship to other well-defined phenotypic traits expressed during melanocyte differentiation (Houghton, A. N., M. Eisinger, A. P. Albino, J. G. Cairncross, and L. J. Old. (1982), Surface antigens of melanocytes and melanomas: Markers of melanocyte differentiation and melanomas subsets, *J. Exp. Med.* 156:1755; Houghton, A. N., F. X. Real, L. J. Davis, C. Cardon-Cardo, and L. J. Old. (1987) Phenotypic heterogeneity of melanoma: Relation to the differentiation program of melanoma cells, *J. Exp. Med.* 164:812), the most distinctive being the synthesis of the pigment melanin within melanosomes.

Clinical observations have suggested that an immune response directed against antigens expressed by normal pigment cells might influence the course of metastatic melanoma. Specifically, Vitiligo and hypopigmentation in patients with melanoma have been associated with a good prognosis (Nordlund, J. J., J. M. Kirkwood, B. M. Forget, G. Milton, D. M. Albert, and A. B. Lerner. (1983) Vitiligo in patients with metastatic melanoma: a good prognosis sign, *J. Am. Acad. Dermatol.* 9:689; Bystryn, J. C., D. Rigel, R. J. Friedman, and A. Kopf. (1987) Prognostic significance of hypopigmentation in malignant melanoma, *Arch. Dermatol.* 123:1053.) In this regard, melanosomal antigens can be recognized by the immune system. This has been demonstrated by immunoprecipitation of a gp75 antigen from autologous melanoma cells by serum IgG antibodies of a patient with metastatic melanoma (Mattes, J. M., T. M. Thomson, L. J. Old, and K. O. Lloyd. (1983) A pigmentation-associated, differentiation antigen of human melanoma defined by a precipitating antibody in human serum, *Int. J. Cancer.* 32:717). The gp75 antigen is a melanosomal polypeptide that is the most abundant glycoprotein synthesized by pigmented melanocytes and melanomas. (Tai, T., M. Eisinger, S. Ogata, and K. O. Lloyd. (1983) Glycoproteins as differentiation markers in human malignant melanoma and melanocytes, *Cancer Res.* 43:2773). Epidermal melanocytes, benign pigmented lesions, and primary and metastatic melanomas express gp75, but other cell types do not (Thomson, T. M., F. X. Real, S. Murakami, C. Cardon-Cardo, L. J. Old, and A. N. Houghton. (1988) Differentiation antigens of melanocytes and melanoma: Analysis of melanosome and cell surface markers of human pigmented cells with monoclonal antibodies, *J. Invest. Dermatol.* 90:459). In the present invention, it is demonstrated that gp75 cDNA had approximately 90% identity with the derived amino acid and nucleotide sequences of a mouse gene that maps to the b (brown) locus. The brown locus is a site that determines coat color and influences the type of melanin synthesized, suggesting that gp75 may regulate or influence the type of melanin synthesized.

The fact that IgG antibodies in sera of a patient with metastatic melanoma have been shown to immunoprecipitate gp75 demonstrates that immunological tolerance against gp75 can be broken. This invention therefore provides expression vectors comprising gp75 cDNA for use as a vaccine against melanoma, whereby the amino acid sequences of peptides were determined from gp75 polypeptide, which was isolated and purified by the mouse monoclonal antibody TA99, and whereby cDNA clones were isolated by screening with oligonucleotides based on the peptide sequences.

SUMMARY OF THE INVENTION

The present invention provides an isolated nucleic acid molecule whose sequence encodes the amino acid sequence for gp75 or a fragment thereof.

The present invention further provides an isolated cDNA molecule of the gp75 nucleic acid molecule as well as an isolated cDNA molecule of a fragment of the gp75 nucleic acid molecule having the nucleotide sequence shown in FIG. 3 and the amino acid sequence derived therefrom.

This invention also provides vaccines for stimulating or enhancing in a subject to whom the vaccine is administered production of antibodies directed against gp75.

This invention further provides a method for stimulating or enhancing in a subject production of antibodies directed against gp75. The method comprises administering to the subject a vaccine of this invention in a dose effective for stimulating or enhancing production of the antibodies.

This invention further provides methods for treating, preventing or delaying recurrence of cancer. The methods comprise administering to the subject a vaccine of this invention in a dose effective for treating, preventing or delaying recurrence of cancer.

Figure 1A:
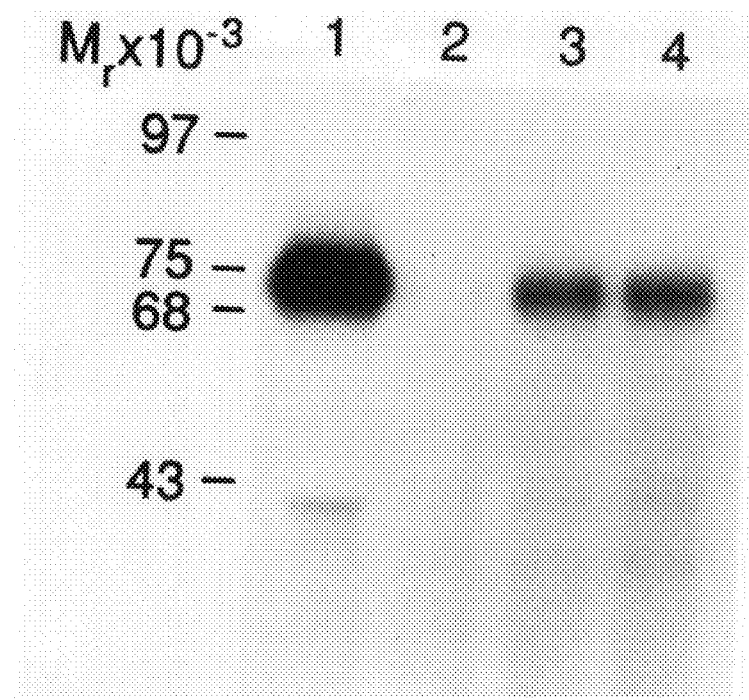
FIG. 1. Immunoprecipitation and peptide composition analysis of proteins recognized by mAb TA99 and AU serum.

A. One-dimensional SDS-PAGE of immunoprecipitates from $^{125}$I-labeled lysates of SK-MEL-19 by mAb TA99 (lane 1), normal human serum (lane 2) and AU sera from 1/75 (lane 3) and from 10/76 (lane 4). B. Bands corresponding to gp75 or to gp75 treated with Endo H (partially deglycosylated) were excised from SDS-polyacrylamide gel and the peptide composition was analyzed by limited digestion with S. aureus V8 protease on SDS-PAGE. –, gp75; +, gp75 partially deglycosylated with Endo H. Autoradiographic exposure was 2 days for TA99 and 5 days for AU peptides.

FIG. 2: Amino acid sequence of three peptides derived from gp75.

The underlined amino acid residues are those that differ from residues predicted from the mouse cDNA pMT4 (Shibahara, S., Y. Tomita, T. Sakakura, C. Nagar, B. Chaudhuri, and R. Muller. (1986) Cloning and expression of cDNA encoding mouse tyrosinase, *Nucleic Acid Res.* 14:2413). Amino acid sequence of three peptides derived from gp75

FIG. 3: Partial cDNA Sequence of gp75.

Depicted is the 5' to 3' partial cDNA fragment from nucleotide 778 to nucleotide 1524.

Figure 4:
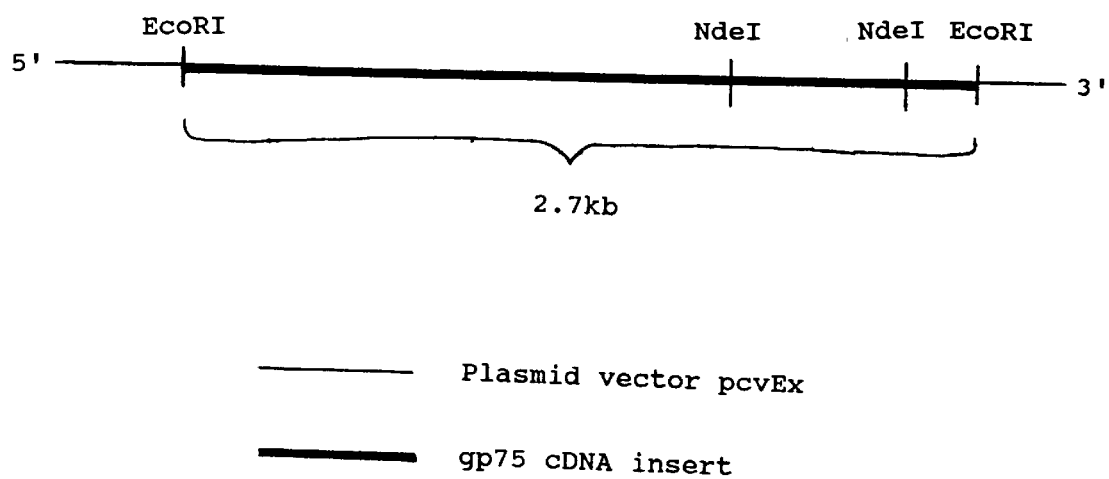

FIG. 4: Isolation of a full length cDNA encoding gp75.

A partial restriction map is represented with a 2.7 kb gp75 cDNA insert. A partial nucleotide sequence containing the first 18 neucleotides of the full 2.7 kb cDNA of GP75 is represented in the 5' to 3' direction.

DETAILED DESCRIPTION OF THE INVENTION

The present invention provides an isolated nucleic acid molecule whose sequence encodes the amino acid sequence for gp75 or a fragment thereof.

The present invention further provides that the amino acid sequence for a fragment of gp75 in one embodiment of the invention is asn-thr-val-glu-gly-tyr-ser-asp-pro-thr-gly-lys-tyr-asp-pro-ala-val. In another embodiment, the amino acid sequence is met-phe-val-thr-ala-pro-asp-asn-leu-gly-tyr-thr-tyr-glu. In still another embodiment, the amino acid sequence is asn-phe-asp-ser-thr-leu-ileu-ser-pro-asn-ser-val-phe-ser.

The present invention further provides an isolated cDNA molecule of the gp75 nucleic acid molecule as well as an isolated cDNA molecule of a fragment of the gp75 nucleic acid molecule having the nucleotide sequence shown in FIG. 3 and the amino acid sequence derived therefrom.

E. coli strain DH5α designated GP75 E-1, containing the pGP75 E-1 plasmid which comprises the plasmid vector designated pcvEx and a full length 2.7 kb GP75 cDNA insert (see FIG. 4), have been deposited with the American Type Culture Collection, 10801 University Boulevard, Manassas, Va. 20110, under ATCC Accession No. 68565. The deposits was made pursuant to the provisions of the Budapest Treaty on the International Recognition of the Deposit of Microorganisms for the Purposes of Patent Procedure (Budapest Treaty).

The plasmid containing the full length 2.7 kb cDNA may be recovered from the deposited E. coli host strains by methods well-known in the art, (Maniatis, T., E. F. Frish, and J. Sambrook, 1989, Molecular Cloning: A Laboratory Manual. Cold Spring Harbor Laboratory, Cold Spring Harbor, N.Y. 1.38–1.39, 1.42–1.343). Isolation of the 2.7 kb GP75 cDNA from the plasmid may be done using a restriction endoneucliase digestion with EcoRI by methods well-known in the art.

Additionally, this invention provides an expression vector comprising a DNA sequence essential for replication of the vector combined with the cDNA molecule of the gp75 nucleic acid molecule or fragment adapted for expression in a host. The expression vector may be vaccinia virus or, preferably, an Imclone vector.

This invention also provides a vaccine for stimulating or enhancing in a subject to whom the vaccine is administered production of antibodies directed against gp75 comprising the expression vector containing the cDNA molecule, an effective amount of an adjuvant and a pharmaceutically acceptable carrier. Preferably, the subject is a human being and the gp75 is bound to the adjuvant. The adjuvant may be a microbial adjuvant or any other pharmaceutical agent.

Further, the present invention provides a vaccine for stimulating or enhancing in a subject to whom the vaccine is administered production of antibodies directed against gp75. The vaccine may comprise the amino acid sequence derived from the cDNA molecule of the gp75 nucleic acid molecule or fragment or an amount of purified gp75 or a fragment thereof effective to stimulate or enhance antibody production in the subject, an effective amount of an adjuvant and a pharmaceutically acceptable carrier. Preferably, the subject is a human being and the gp75 is bound to the adjuvant. The adjuvant may be a microbial adjuvant or any other pharmaceutical agent.

This invention also provides a method for stimulating or enhancing in a subject production of antibodies directed against gp75. The method comprises administering to the subject a vaccine of this invention in a dose effective for stimulating or enhancing production of the antibodies.

This invention further provides a method for treating cancer in a subject affected with cancer. The method comprises administering to the subject a vaccine of this invention in a dose effective for treating cancer.

This invention still further provides a method for preventing cancer in a subject affected with cancer. The method comprises adminstering to the subject a vaccine of this invention in a dose effective for preventing cancer. This invention also provides a method for delaying the recurrence of cancer in a subject susceptible to cancer. The method comprises adminstering to the subject a vaccine of this invention in a dose effective for delaying the recurrence of cancer.

The methods of treating, preventing and delaying recurrence of cancer may be directed to a cancer such as melanoma. The vaccines are useful in preventing cancer such as melanoma in patients at high risk for recurrent or primary melanoma.

In these methods, the gp75 may be bound to the adjuvant. Additionally, an effective amount of cyclophosphamide may be administered to the subject prior to administering the vaccine.

This invention is illustrated in the Experimental Detail section which follow. These sections are set forth to aid in an understanding of the invention but are not intended to, and should not be construed to, limit in any way the invention as set forth in the claims which follow thereafter.

EXPERIMENT 1

MATERIALS AND METHODS

Tissue culture:

The melanoma cell line SK-MEL-19 was grown in MEM plus 1% non-essential amino acids and penicillin and streptomycin, except that SerumPlus 10% (v/v) (Hazelton Research Products Inc., Lenexa, Kan.) was substituted for fetal calf serum (FCS).

Isolation and purification of gp75:

Post-nuclear membrane fraction from melanoma cell line SK-MEL-19 was isolated by homogenization of cells in 20 mM Tris/HCl, pH 7.5, 5 mM $MgCl_2$, 2 mM PMSF and centrifugation at 10,000×g. The membranes were solubilized in 20 mM Tris/HCl, pH 7.5, 3 M KCl and 5 mM EDTA and centrifuged at 100,000×g. Insoluble protein fraction was resuspended in 20 mM Tris/HCl pH 7.5, 0.5% sodium deoxycholate. Detergent soluble proteins were collected by centrifuging at 100,000×g. The supernatant was dialyzed against 20 mM Tris/HCl, pH 7.5, 0.15 M NaCl and 2 mM CHAPS and applied to a Mono Q (HR 5/5, Pharmacia LKB Biotechnology Inc. Piscataway, N.J.) column equilibrated with 20 mM Tris/HCl, pH 7.5, 0.15 M NaCl and 2 mM (3-[(3-cholamidopropyl)dimethyl-ammonio] 1-propanesulfonate (CHAPS) (buffer A). Bound proteins were eluted with a linear gradient of 0–1.0 M NaCl in buffer A. Fractions were assayed for gp75 by a competitive inhibition assay. Fractions containing gp75 were pooled, dialyzed against Con A column buffer (10 mM Tris/HCl, pH 7.5, containing 1 mM $CaCl_1$, 1 mM $MnCl_2$ and 2 mM PMSF) and applied to Con A-Sepharose column. Unbound proteins were removed by washing with column buffer. Proteins bound to Con A were eluted with 0.25 M α-D-methylmannopyranoside in Con A column buffer. Fractions containing gp75 were pooled and dialyzed against 10 mM Tris/HCl, pH 7.5, 2 mM CHAPS and 2 mM PMSF (CB) and applied to a mouse monoclonal antibody (mAb) TA99 (Thomson, T. M., J. M. Mattes, L. Roux, L. J. Old, and K. O. Lloyd (1985) Pigmentation-associated glycoprotein of human melanoma and melanocytes: Definition with a mouse monoclonal antibody, *J. Invest. Dermatol.* 85:169) Affi-Gel 10 affinity column. The gel was washed sequentially, with 6 ml each of CB, CB+1 M NaCl, CB, and CB+2 mM CHAPS. Bound gp75 was eluted from the column with 0.1 M glycine-HCl, pH 3.1, containing 2 mM CHAPS.

Competitive inhibition assay for gp75:

During purification, gp75 was monitored and quantitated by measuring the ability of fractions to inhibit the binding of 300 ng/ml mAb TA99 to SK-MEL-19 cells fixed in methanol: acetone (1:1 vol/vol) by enzyme immunoassay (ELISA) (Houghton, A. N., H. Brooks, R. J. Cote, M. C. Taormina, H. F. Oettgen and L. J. Old (1983) Detection of cell surface and intracellular antigens by human monoclonal antibodies: hybrid cells derived from lymphocytes of patients with malignant melanoma, *J. Exp. Med.* 158:53).

Immunoprecipitation, gel electrophoresis and peptide mapping:

Iodination of Con A-Sepharose bound protein fraction of SK-MEL-19 by chloramine T method and immunoprecipitation with mAb TA99 and AU serum was done as described (Mattes, J. M., T. M. Thomson, L. J. Old, and K. O. Lloyd. (1983) pigmentation-associated, differentiation antigen of human melanoma defined by a precipitating antibody in human serum, *Int. J. Cancer.* 32:717). Proteins were analyzed by SDS-polyacrylamide gel electrophoresis (SDS-PAGE) (Laemmli, U. K. (1970) Cleavage of structural proteins during assembly of the head of bacteriophage T4, *Nature.* 227:680). For endoglycosidase H (Endo H) digestion, the immunoprecipitates were suspended in 0.4% SDS, heated at 100° for 5 minutes and digested with 1 mU of Endo H (Genzyme Corporation, Boston, Mass.) in 100 mM citrate buffer, pH 5.5 for 16 h at 37°. Two-dimensional electrophoresis using ampholines pH 5–7 (LKB-Produkter, Bromma, Sweden) was performed according to O'Farrel (O'Farrel, P. H. (1975) High resolution two-dimensional electrophoresis of proteins, *J. Biol. Chem.* 250:4007). Peptide mapping of immunoprecipitated gp75 was performed by limited proteolysis with *Staphylococcus aureus* V8 protease (V8 protease) (Boehringer Mannheim Biochemicals. Indianapolis, Ind.) in SDS-PAGE according to Cleveland et al. (Cleveland, D. W., S. G. Fischer, M. W. Kirschner, and U. K. Laemmli. (1977) Peptide mapping by limited proteolysis in sodium dodecyl sulfate and analysis by gel electrophoresis. *J. Biol. Chem.* 252:1102).

Peptide sequencing:

Peptide sequencing was performed at the Harvard University Microchemistry Facility. Purified gp75 (12 μg) electroblotted onto nitrocellulose was digested with V8 protease (1:20 w/w) according to Aebersold (Aebersold, R. H., J. Leavitt, R. A. Saavedra, and L. E. Hood. (1987) Internal amino acid sequence analysis of proteins separated by one- and two-dimensional gel electrophoresis after in situ protease digestion on nitrocellulose, *Proc. Natl. Acad. Sci. USA.* 84:6970) and resulting peptides were separated on a Brownlee RP-300 2.1×100 mm C8 column at 38° C. Several peaks from the V8 protease digest were pooled and dried. Complete reduction and alkylation was performed by addition of 50 μl of 8 M urea/0.4 M ammonium bicarbonate buffer, pH 8.0, 5 μl of 100 mM dithiothreitol and heating at 50° C. for 15 minutes. The sample was then incubated with 5 μl of 45 mM iodoacetic acid for 15 minutes at room temperature and diluted with 140 μl distilled water. Further digestion of reduced and alkylated peptide fraction with trypsin (1:25 w/w) was carried out overnight at 37° C. Fractions to be sequenced were directly applied to polybrene precycled glass fiber filters and sequenced on an ABI 477A protein sequencer. Amino acids were separated with an ABI 120A online HPLC. For each peptide a minimum of 20 cycles was performed. The repetitive yield of the HPLC under routine laboratory conditions was 93%. The amino acid sequences of only those peptides with highest confidence results are reported.

Cloning and Sequencing of gp75 cDNA:

a cDNA library was constructed from a melanoma cell line SK-MEL-19. Oligonucleotide probe was used to isolate a gp75 cDNA clone according to methods previously described. (Bouchard, B., B. Fuller, S. Vijayasaradhi, and A. N. Houghton. (1989) Induction of pigmentation in mouse fibroblasts by expression of human tyrosinase, *J. Exp. Med.* 169:2029). The sequence of the oligonucleotide probes was:

5' CTCGAAGGTGAAGCCCAGGT-TGTCGGGGGCGGTCACGAACATCTC 3'. A 2.0-kb cDNA clone, designated GP75-1, was sequenced (Stratagene Cloning Systems, La Jolla, Calif.). The nucleotide sequence of GP75-1 has been deposited with EMBL data bank under the accession number X51455. (See FIG. 3)

RESULTS AND DISCUSSION

Both mouse mAb TA99 and serum from melanoma patient AU immunoprecipitate a 75-kDa antigen, and mAb TA99 preclears the gp75 antigen precipitated by AU serum (Thomson, T. M., J. M. Mattes, L. Roux, L. J. Old, and K. O. Lloyd (1985) Pigmentation-associated glycoprotein of human melanoma and melanocytes: Definition with a mouse monoclonal antibody, *J. Invest. Dermatol.* 85:169). Since mAb TA99 was used to purify gp75 from the melanoma cell line SK-MEL-19, it was important to confirm that mAb TA99 detected only the gp75 antigen recognized by AU serum. In previous studies, we had shown that mAb TA99 does not react with human tyrosinase, a 75–80 kDa glycoprotein also expressed in pigmented melanocytes (Bouchard, B., B. Fuller, S. Vijayasaradhi, and A. N. Houghton. (1989) Induction of pigmentation in mouse fibroblasts by expression of human tyrosinase, *J. Exp. Med.* 169:2029). However, from these experiments, we could not rule out the possibility that mAb TA99 cross-reacts with other polypeptides expressed by SK-MEL-19.

Figure 1B:
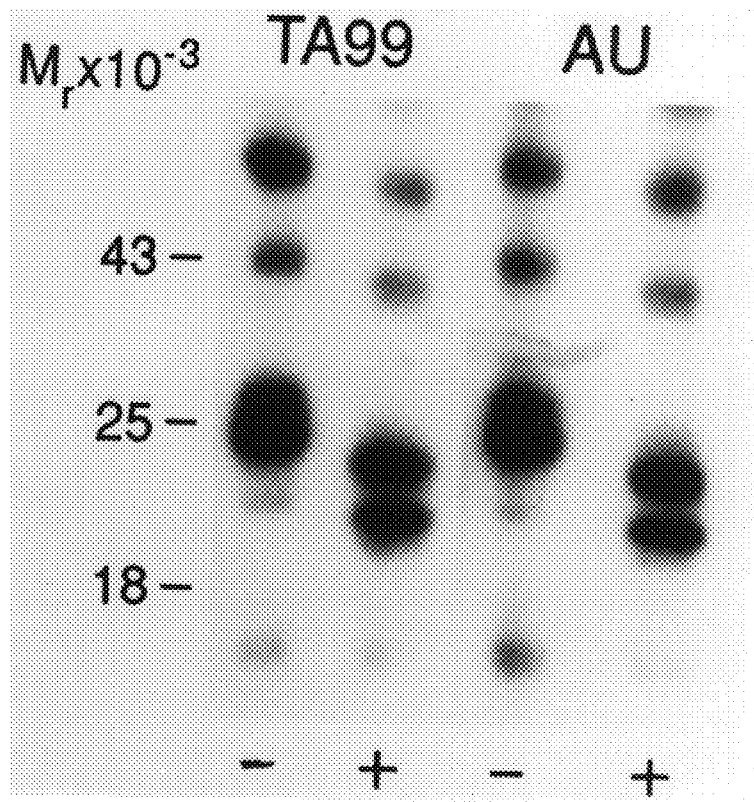

Proteins immunoprecipitated by mAb TA99 and AU serum antibody were analyzed by one- and two-dimensional SDS-PAGE and by peptide maps using limited proteolysis with *S. aureus* V8 protease. Proteins precipitated with both mAb TA99 and AU serum antibodies had identical molecular mass (75 kDa), isoelectric point (5.5–5.9), and peptide composition (FIG. 1), confirming that TA99 and AU serum recognized the same gp75 molecule.

The gp75 antigen was purified as described in Materials and Methods. Affinity purified gp75 was utilized for peptide sequencing. The amino acid sequences of three internal peptides were obtained by proteolytic cleavage of purified gp75 with V8 protease and trypsin. The sequences of the three peptides are shown in FIG. 2. There was 90% identity with amino acid sequences deduced from the mouse cDNA, clone, pMT4, isolated by Shibahara et al. (at amino acid positions 247–260, 333–349, and 428–441 of pMT4) (Shibahara, S., Y. Tomita, T. Sakakura, C. Nagar, B. Chaudhuri, and R. Muller. (1986) Cloning and expression of cDNA encoding mouse tyrosinase, *Nucleic Acid Res.* 14:2413). Oligonucleotide probes were derived from peptide sequences of gp75 and used to screen a cDNA library constructed from the human melanoma cell line SK-MEL-19. Two cDNA clones (1.8 and 2.0 kb) were isolated from a cDNA library of SK-MEL-19. Partial nucleotide sequences of the cDNA clones (GP-75-1 and -2), one of which is shown in FIG. 3, showed 88.6% identity with pMT4 (between nucleotides 649–1437 within the open reading frame). The derived amino acid sequence of GP75-1 and 2 showed 93.6% identity with the derived amino acid sequence of pMT4 between amino acid residues 219–467. There was 55.3% identity between the cDNA sequences of gp75 and human tyrosinase (Bouchard, B., B. Fuller, S. Vijayasaradhi, and A. N. Houghton. (1989) Induction of pigmentation in mouse fibroblasts by expression of human tyrosinase, *J. Exp. Med.* 169:2029) between nucleotides 618–1344 of tyrosinase.

The close homology between human gp75 and the deduced product of the mouse pMT4 gene sheds some light on the possible structure and function of gp75. The pMT4 clone was isolated from mouse melanocytic cells (Shibahara, S., Y. Tomita, T. Sakakura, C. Nagar, B. Chaudhuri, and R. Muller. (1986) Cloning and expression of cDNA encoding mouse tyrosinase, *Nucleic Acid. Res.* 14:2413). Originally pMT4 cDNA was thought to code for mouse tyrosinase, which maps to the mouse c (albino) locus. However, further studies showed that pMT4 is distinct from mouse tyrosinase (Yamamoto, H., S. Takeuchi, T. Kudo, K. Makino, A. Nakata, T. Shinoda, and T. Takeuchi. (1987) Cloning and sequencing of mouse tyrosinase cDNA, *Jpn. J. Genetics.* 62:271; Muller, G., S. Ruppert, E. Schimd, and G. Schutz (1988) Functional analysis of alternatively spliced tyrosinase gene transcripts, *EMBO (Eur. Mol. Biol. Organ. J.)* 7:2723; Jackson, I. J. (1988) A cDNA encoding tyrosinase-related protein maps to the brown locus in mice, *Proc. Natl. Acad. Sci. USA.* 85:4392). Likewise, the sequence of gp75 is distinct from the sequence of human tyrosinase, although there is limited identity (43.1%) between gp75 and the derived amino acid sequence of human tyrosinase (between amino acid residues 208–459). The function of gp75 and the pMT4 product is suggested by the finding that pMT4 maps to the b (brown) locus in the mouse (Jackson, I. J. (1988) A cDNA encoding tyrosinase-related protein maps to the brown locus in mice *Proc. Natl. Acad. Sci. USA.* 85:4392), a region that regulates coat color (Silvers, W. K. (1979) Comparative genetics of coat colour in mammals, In: *The Coat Colors in Mice*, Springer Verlag, New York. 1). The homology between gp75 and the deduced amino acid sequence of pMT4 permits the formal identification of the human homologue of the mouse brown locus gene product. Based on its melanosomal localization and structural similarity to tyrosinase, the gp75 molecule may regulate melanin synthesis, and determine the type of melanin synthesized.

It has been perceived that melanosomal determinants and other intracellular antigens are not potential targets for immunotherapy of melanoma. However, recently it has become evident that intracellular proteins can be processed and presented as peptides to cytotoxic T cells (CTL) by antigen-presenting cells (Townsend, A. R. M., and H. Bodmer. (1989) Antigen recognition by class I-restricted T lymphocytes, *Ann. Rev. Immunol.* 7:601). This finding opens up the theoretical possibility that T cell responses against melanoma could be directed against molecules expressed within the tumor cell. Alternatively, melanosomal components, which are normally transported outside the melanocyte during maturation, could accumulate in the extracellular space around tumor cells, or local tissue necrosis could lead to release and deposition of intracellular products. In support of the accessibility of gp75, radiolabeled TA99 mAb specifically localizes to human melanoma xenografts in nu/nu mice (Welt, S., J. M. Mattes, R. Grano, T. M. Thomson, R. W. Leonard, P. B. Zanzonico, R. E. Bigler, S. Yeh, H. F. Oettgen, and L. J. Old. (1987) Monoclonal antibody to an intracellular antigen images human melanoma transplants in nu/nu mice, *Proc. Natl. Acad. Sci. USA.* 84:4200), indicating the availability of the antigen to antibody within tumor sites.

IgG antibodies in the melanoma patient AU recognized determinants on gp75 that were shared by melanoma cells and normal melanocytes (Mattes, J. M., T. M. Thomson, L. J. Old, and K. O. Lloyd. (1983) A pigmentation-associated, differentiation antigen of human melanoma defined by a precipitating antibody in human serum, *Int. J. Cancer.* 32:717). With the isolation of cDNA clones that code for gp75, it should be possible to study strategies for active immunization against gp75. There are at least two requirements for effective induction of CTL responses to gp75: 1) immune tolerance to gp75 must be broken, and 2) gp75 peptides must be processed and effectively presented by major histocompatibility antigens on melanoma cells. Alternatively, it is possible that differentiation antigens of melanocytes could carry unique determinants. Genes encoding products expressed by normal melanocytes could be mutated or rearranged during malignant transformation, generating novel epitopes for recognition by CTL and antibodies. In this regard, the best characterized unique antigen on human melanoma cells is a determinant on melanotransferrin, a 95–97 kDa glycoprotein expressed on cultured melanocytes and melanoma cells (Real, F. X., M. J. Mattes, A. N. Houghton, H. F. Oettgen, K. O. Lloyd, and L.

J. Old. (1984) Class 1 (unique) antigens of human melanoma. Identification of a 90,000 dalton cell surface glycoprotein by autologous antibody, *J. Exp. Med.* 160:1219; Furakawa, K. S., K. Furakawa, F. X. Real, L. J. Old, and K. O. Lloyd. (1989) A unique antigenic epitope of human melanoma is carried on the common melanoma glycoprotein gp75/p97, *J. Exp. Med.* 169:585). In support of this possibility, genetic alterations have been detected at high frequency and widely throughout the genome of human melanoma cells. (Dracopoli, N. C., A. N. Houghton, and L. J. Old. (1985) Loss of polymorphic restriction fragments in malignant melanoma: Implications for tumor heterogeneity, *Proc. Natl. Acad. Sci. USA.* 82:1470; Dracopoli, N. C., B. Alhadeff, A. N. Houghton, and L. J. Old. (1987) Loss of heterozygosity at autosomal and x-linked loci during tumor progression in a patient with melanoma, *Cancer Res.* 47:3995).

EXPERIMENT 2

MATERIALS AND METHODS

Isolation of the 2.7 kb GP75 cDNA in λ phage:

The 2.0 Kb GP75 cDNA fragment described in experiment 1 (for sequence see FIG. 3) was used to screen a genomic library. A genomic clone which contained the GP75 gene was obtained.

cDNA library construction and screening:

A cDNA Library was constructed from 3 μg of poly(A)+ selected mRNA (Maniatis, T., E. F. Frish, and J. Sambrook. 1982. Molecular Cloning: A Laboratory Manual. Cold Spring Harbor Laboratory, Cold Spring Harbor, N.Y. 545 pp.) prepared from the human melanotic melanoma cell line SK-MEL-19 (Houghton, A. N., M. Eisinger, A. P. Albino, J. G. Cairncross, and L. J. Old. 1982. Surface antigens of melanocytes and melanoma: markers of melanocyte differentiation and melanoma subsets. *J. Exp. Med.* 156:1755). Full-length cDNA was synthesized, rendered blunt ended using Klenow enzyme, and tailed with Eco RI linkers (New England Biolabs, Inc. Beverly, Mass.) (Gubler, U., and B. J. Hoffman. 1983. A simple and very efficient method of generating cDNA libraries. *Gene (Amst.).* 25:263). The cDNA was then size fractionated on Ultrogel Aca 34 (Pharmacia Fine Chemicals, Piscataway, N.J.) (Watson, C. J., and J. F. Jackson. 1985. Constructing and screening cDNA libraries in λgt 10 and λgt 11. In DNA Cloning: A Practical Approach. D. M. Glover, editor. IRL Press Limited, Oxford. 79–100). cDNA molecules>800 bp were used to construct a library of $3 \times 10^5$ recombinants in the λ phage vector gt10 (Huynh, T. V., R. A. Young, and R. W. Davis. 1985. An alternative procedure for the synthesis of double stranded cDNA for cloning in phage and plasmid vectors. In DNA Cloning: A Practical Approach. D. M. Glover, editor. IRL Press Limited, Oxford. 49–78).

For screening a fragment based on the 5' terminal coding region of the genomic clone obtained above was used. The 2.7 kb cDNA in λ phage was obtained. (Bouchard, B., B. Fuller, S. Vijayasaradhi, and A. N. Houghton. (1989) Induction of pigmentation in mouse fibroblasts by expression of human tyrosinase, *J. Exp. Med.* 169:2029).

Recovery of the 2.7 kb cDNA:

Restriction endonuclease digestion with Eco RI was performed on the 2.7 kb cDNA GP75 insert. The DNA was purify by extraction with phenolchloroform and ethanol precipitation. The DNA was redissolve in TE (pH 7.6) at a concentration of 100 μg/ml. Ligation of the cohesive termini was done by the following method. The following ligation mixtures were set up: 1) 0.1 μg of the pcvEx vector DNA was transferred to a sterile microfuge tube. An equimolar amount of 2.7 kb GP75 cDNA was added. 2) $H_2O$ was added to 7.5 μl, and the solution was warmed to 45° C. for 5 minutes to melt any cohesive termini that have reannealed. The mixture was chill to 0° C. 3) then add 1 μl of 10×bacteriophage T4 DNA ligase buffer (200 mM Tris.Cl (pH 7.6), 50 mM $MgCl_2$, 50 mM dithiothreitol, 500 μg/ml bovine serum albumin (Fraction V; Sigma)), 0.1 Weiss unit of bacteriophage T4 DNA ligase, and 1 μl of 5 mM ATP. The reactions were incubated for 1–4 hours at 16° C. The plasmid pGP75 E-1 depicted in FIG. 4, which contains the plasmid vector pcvEx and the 2.7 kb GP75 cDNA insert, was obtained.

Creating competent *E. coli*:

1–2 μl of each of the ligation reactions were used to transform competent *E. coli* by the following method. First inoculate 5 ml of LB with single colony from fresh overnight plate. Then grow up the cells for 5–7 hours in a shaker. Next inoculate 1 liter of LB in 4 liter flask with 4 ml of the above. Grow to an $O.D._{550}=0.15$. Spin down for 10 min. at 3 K and resuspend in 400 ml of 100 mM $CaCl_2$ at 0° C. Then spin down again for 10 min. at 3 K and resuspend in 10 ml of 100 mM $CaCl_2$ at 0° C. Add 2.5 ml of 80% glcerol.

Transformation of DH5α *E. coli*:

1–20 μl the GP75 E-1 plasmid was added to 100 μl competent cells. This was kept on ice for 20 min. Then heat shock for 1 min. at 42° C. Then returned to the ice for 10 min. The cells were spun for 10 seconds in microfuge and resuspend in 200 μl of LB. This was incubated for 45 min. at 37° C. on a shaker.

The resulting *E. coli* containing the pGP75 E-1 plasmid was deposited with the ATCC.

EXPERIMENT 3

MATERIALS AND METHODS

Reagents:

L-[ring-3,5-$^3$H]tyrosine (specific activity 46.7 Ci/mmol) was obtained from ICN (Irvine, Calif.). Concanavalin A-Sepharose and protein A Sepharose CL 4B were from Pharmacia (Piscataway, N.J.). Affigel-10 was from Bio-Rad (Richmond, Calif.). All electrophoretic chemicals were from BRL (Gaithersburg, Md.). Deoxycholic acid (sodium salt), Nonidet P-40, (3-[(3-cholamidopropyl)dimethyl-ammonio] 1-propanesulfonate (CHAPS), phenylmethanesulfonyl fluoride (PMSF) and α-D-methylmannopyranoside, alkaline-phosphate-conjugated goat anti-mouse IgG, alkaline phosphatase color development reagent and all other reagent-grade chemicals were from Sigma (St. Louis, Mo.). HPLC-grade water and other reagent-grade organic solvents were from Fisher (Pittsburgh, Pa.). Mouse MAbs TA99 ($IgG_{2A}$) and F23 ($IgG_{2a}$) were purified using protein A Sepharose. TA99 MAb is an anti-gp75 antibody (Thomson, T. M., Mattes, J. M., Roux, L., Old, L. J. and Lloyd, K. O., Pigmentation-associated glycoprotein of human melanoma and melanocytes: definition with a mouse monoclonal antibody, *J. invest. Dermat.,* 85, 169–174, 1985) and MAb F23, used as control antibody, is an anti-human colon carcinoma antibody that does not react with human melanocytic cells.

Tissue culture:

The melanoma cell line SK-MEL-19 was grown and passaged in MEM supplemented with 10% Serum Plus (Hazelton, Lenexa, Kans.) as described by Vijayasaradhi, S., Bouchard, B. B. and Houghton, A. N., The melanoma antigen gp75 is the human homologue of mouse b (brown) locus gene, *J. exp. Med.,* 171, 1375–1380 (1990).

Isolation and purification of gp 75:

All procedures for the purification of gp75 were carried out at 0–5° C. unless otherwise specified. Semi-confluent SK-MEL-19 Melanoma cells were harvested from 150-cm$^2$ flasks by scraping with a rubber policeman, collected into tissue culture medium and centrifuged, after which the cells (60-g pellet) were washed with PBS. The cells were suspended in 300 ml 20-mM Tris/HCl, pH 7.5, 5 mM MgCl$_2$, 2 mM PMSF for 10 min and homogenized in a Dounce homogenizer. Cell lysis was monitored by phrase-contrast microscopy. The homogenate was centrifuged at 1,000 g for 10 min, then the supernatant was collected and centrifuged at 10,000 g for 30 min. The crude membrane pellet was suspended in 50 ml 20 mM Tris/HCl, pH 7.5, 3 M KCl and 5 mM EDTA, gently homogenized in a Dounce homogenizer and centrifuged at 100,000 g for 90 min. The pellet was resuspended in 30 ml 20 mM Tris/HCl pH 7.5, 0.5% sodium deoxycholate and gently homogenized. The homogenate was centrifuged at 100,000 g and the supernatant was dialyzed against 200–300 vol of 20-mM Tris/HCl, pH 7.5, 0.15 M NaCl and 2 mM CHAPS for 24 hr. The dialysate was clarified by centrifugation at 100,000 g for 90 min. The clear supernatant from this step was applied to a Mono Q (Pharmacia, HR 5/5) column equilibrated with 20 mM Tris/HCl, pH 7.5, 0.15 M NaCl and 2 mM CHAPS (buffer A), via Superloop (Pharmacia) at a flow rate of 0.5 ml/min. The column was washed with 10 ml buffer A, bound proteins were eluted with a 30-ml linear gradient of 0–1.0 M NaCl in buffer A and 1 ml fractions were collected. Fractions were assayed for gp 75 by a competitive inhibition assay and positive fractions were pooled and dialyzed against 100 vol of C on A column buffer, 10 mM Tris/HCl, pH 7.5, containing 1 mM CaCl$_2$, 1 mM MnCl$_2$ and 2 mM PMSF, for 18 hr.

Con A-Sepharose chromatography:

Con A-Sepharose (5 ml) was washed with 50 ml Con A column buffer in 10 ml Econo-column (Bio-Rad) and the pooled, dialyzed fractions from mono Q ion-exchange chromatography were applied to the column at a flow rate of 1.0–1.5 ml/min. The effluent was reapplied to the column and the column was washed with the column buffer until the absorbance (280 nm) of the effluent was below 0.01. Proteins bound to Con A were eluted with 0.25 M $\alpha$-D-methylmannopyranoside in Con A column buffer and 1.5–2 ml fractions were collected. Incubation of the column with elution buffer for 15–20 min at 25–30° C. prior to elution improved the yield of protein. Fractions containing gp75 were pooled and dialyzed against 10 mM Tris/HCl, pH 7.5. 2 mM CHAPS and 2 mM PMSF and applied to TA99 Affi-Gel 10 affinity column.

TA99 affinity chromatography:

TA99 MAb was purified from ascites of (BALB/cx C57BL/6) F$_1$ mice by ammonium sulfate precipitation followed by chromatography over protein A-Sepharose and Sephadex G-25 columns. Affi-Gel 10 was prepared for coupling according to the manufacturer's instructions and washed with cold coupling buffer (CB), 50 mM HEPES, pH 7.6, 150 mM NaCl. The coupling reaction was carried out at 4° C. for 4 hr with 9 mg purified TA99 IgG per 2 ml Affi-Gel in a total volume of 6 ml coupling buffer. Uncoupled sites were blocked by incubating with an equal volume of 0.1 M ethanolamine HCl, pH 8.0 for 1 hr at 4° C. The gel was then washed sequentially, with CB, CB+1.5 M NaCl, CB, and finally with 10 mM Tris/HCl, pH 7.5, 0.15 M NaCl and 2 mM CHAPS. The coupling efficiency was determined by measuring the antibody titer of TA99 in the clear supernatant of coupling reaction by ELISA against SK-MEL-19 melanoma cells before and after the 4-hr coupling reaction. The coupling efficiency was 60–80% and approximately 5 mg of TA99 IgG were coupled per ml of Affi-Gel 10. Pooled and dialyzed protein solution from Con A chromatography was applied to 2 ml MAb TA99-Affi-Gel 10 column at 0.5 ml/min flow rate and the effluent was reapplied to the column. The gel was then washed sequentially, with 6 ml each of CB, CB+1 M NaCl, CB, and CB+2 mM CHAPS. Bound gp75 was eluted from the column with 0.1 M glycine-HCl, pH 3.1 containing 2 mM CHAPS.

Enzyme-linked immunosorbent assay for gp75:

For ELISA, trypsinized cells were plated at 500–2000 cells/well in micro-well plates (Microtest Plates 3034, Falcon, Oxnard, Calif.) and grown for 48–72 hr at 37° C. in 5% CO$_2$ in a humidified tissue culture incubator. The plates were washed with PBS, fixed with chilled (−20° C.) methanol:acetone (1:1 v/v) for 10 min and then washed 3 times with cold PBS containing 0.2% sodium azide. Plates with the fixed and permeabilized cells were stored at 4° C. TA99 antibody titer was determined on freshly fixed plates, by ELISA. (No significant change was observed in the titer with MAb TA99 upon storage of the plates at 4° C. up to 6 months.) Briefly, the cells were incubated with MAb TA99, 10 $\mu$l per well, and serially diluted in PBS containing 5% gamma-globulin-free FBS (GGFFBS) for 45 min, then plates were washed 3 times with PBS containing 2% GGFFBS and alkaline-phosphatase-conjugated goat anti-mouse IgG (diluted 1:200 in PBS with 5% GGFFBS) was added to each well and incubated for 45 min. Plates were washed 3 times as above and 18 $\mu$l alkaline phosphatase substrate solution (p-phenyl disodium phosphate in diethanolamine buffer, pH 9.8. 5 mM MgCl$_2$) were added. Following 15–20 min incubation at 37° C. in a humidified chamber, the optical density was measured at 405 nm in an Artek (Chantilly, Va.) microplate reader (Model 210).

Competitive inhibition assay for gp75:

During the initial steps, purification of gp75 was monitored and quantitated by measuring the ability of fractions to inhibit the binding of MAb TA99 to SK-MEL-19 cells by ELISA as described above. Subcellular fractions or fractions from column chromatography were serially diluted in 96-well Microtest plates. TA99 antibody was added to a final concentration of 300 ng/ml (just below saturation binding to SK-MEL-19). The antigen-antibody mixture was incubated at room temperature for 30 min and then applied to SK-MEL-19 cells in micro-well plates. The amount of MAb TA99 bound to SK-MEL-19 cells was measured by ELISA as described above. One unit of activity of gp75 was defined as the amount of protein required for half-maximal inhibition of MAb TA99 (300 ng/ml) binding to SK-MEL-19 cells.

Gel electrophoresis and electroblotting:

Proteins were analyzed by SDS-polyacrylamide gel electrophoresis (Laemmli, U. K., Cleavage of structural proteins during assembly of the head of bacteriophage T4, *Nature* (Lond.), 227, 680–685, 1970) and visualized by silver staining (Oakley, B. R., Kirsch, D. R. and Morris, N. R., A simplified ultrasensitive silver stain for detecting proteins in acrylamide gels, *Anal. Biochem.*, 105, 361–363, 1980). Proteins were electroblotted in a Transphor apparatus (Hoefer, San Francisco, Calif.) onto PVDF (polyvinylidene difluoride) membrane (Immobilon, Millipore, Bedford, Mass.) for N-terminal sequencing and analysis of amino-acid composition as described by Matsudaira, P., Sequence from picomole quantities of proteins electroblotted on to polyvinylidene difluoride membranes, *J. biol. Chem.*, 262, 10035–10038, 1987.

Amino acid analysis:

Amino-acid analysis of protein sample transferred to PVDF membrane was carried out at the Harvard University Microchemistry Facility. The protein (0.6 $\mu$g and 0.8 $\mu$g) was hydrolyzed in 6 N HCl for 24 hr at 110° C. Free amino acids were derivatized with phenylisothiocynate and the resulting phenylthiocarbamyl aminoacids were analyzed by HPLC as described by Ebert, R. F., Amino acid analysis by HPLC: optimized conditions for chromatography of pheylthiocarbamyl derivatives, *Anal. Biochem.*, 154, 431–435, 1986.

Immunoprecipitation analysis for tyrosine hydroxylase activity:

Aliquots of 100 µg of detergent-solubilized (1% NP40 in PBS) melanoma (SK-MEL-19) cell extracts were incubated with 3–15 µg of MAb TA99 (anti-gp75), MAb F23 or PBS in a total volume of 45 µl at 4° C. with continuous mixing for 90 min. Protein A Sepharose CL 4B was added to a final concentration of 6 mg/ml. Following 2 hr incubation at 4° C., the supernatants were collected by centrifuging at 15,000 rpm for 5 min at 4° C. The pellets were washed 5 times with PBS containing 1% NP40 and suspended in 50 µl of the same buffer. Tyrosine hydroxylase activity was measured in supernatants and pellets. Approximately 85% of the total tyrosine hydroxylase activity present in the cell extracts prior to addition of protein A Sepharose was reproducibly recovered in the supernatants of PBS control. Enzyme activity recovered in the supernatants of cell extracts incubated with antibody and protein A Sepharose is expressed as percentage activity recovered in PBS control.

Tyrosine hydroxylase assay:

Tyrosine hydroxylase activity was assayed as described by Pomerantz, S. H., L-Tyrosine-3,5-H assay for tyrosinase development in skin of newborn hamsters, *Science*, 164, 838–839, 1969 with minor modifications (Bouchard, B., Fuller, B., Vijayasaradhi, S. and Houghton, A. N., Induction of pigmentation in mouse fibroblasts by expression of human tyrosinase, *J. exp. Med.*, 169, 2029–2042, 1989). One unit of enzyme activity was defined as the amount of protein required to release 1 µmole of $^3H_2O$ from $^3H$ tyrosine in 1 hr at 37° C.

Protein determination:

Protein concentration was estimated by the dye binding method (Bradford, M., A rapid and ultrasensitive method for the quantitation of microgram quantities of protein utilizing the principle of protein-dye binding, *Anal. Biochem.*, 72, 248–254, 1976) using the Bio-Rad Protein Assay system. Purified gp75 was quantitated by approximation of the staining intensity of the protein band on the polyacrylamide gel to a series of known amounts (10–100 ng/protein band) of silver-stained molecular weight marker proteins.

Results and Discussion

The post-nuclear membrane fraction of the melanoma cell line SK-MEL-19 was utilized as a source of gp75 antigen. The membrane fraction was treated with high salt (3 M KCl), and the high-salt-insoluble fraction was then solubilized in the detergent deoxycholate. All subcellular fractions, except the nuclear pellet, were assayed for the presence of gp75 by a competitive ELISA which measured inhibition of MAb TA99 binding to SK-MEL-19 cells (gp75 activity), gp75 was detected only in the deoxycholate-soluble membrane fraction but not in the high-salt-soluble fraction. This is consistent with an integral membrane localization of gp75. The melanosomal membrane localization of gp75 was shown by metabolic pulse-chase labelling of melanoma cells with $^{35}S$-methionine followed by discontinuous sucrose density gradient fractionation (to enrich melanosomes), and immunoprecipitation analysis. In these experiments gp75 could be immunoprecipitated only from detergent-solubilized, pigmented gradient fractions containing melanosomes.

Initial enrichment of gp75 was carried out by fractionation of the deoxycholate-soluble membrane fraction on a Mono Q (anion exchange) column. Bound gp75 eluted between 0.26–0.5 M NaCl as a broad peak of activity, which indicated a charge microheterogeneity. This was confirmed by two-dimensional SDS-PAGE (pI 5.5–5.9). It was observed that the presence or absence of the zwitterionic detergent 3-[(3-cholamidopropyl) dimethyl-ammonio]1-propanesulfonate (CHAPS) in the column equilibration buffer and in the sample buffer did not affect binding of gp75 to the Mono Q column, but addition of CHAPS to the elution buffer improved the yield of gp75.

Mono Q fractions containing gp75 activity were pooled, dialyzed in concanavalin A (Con A) column buffer and applied to a Con A-Sepharose column. Approximately 60% of applied protein was bound to Con A. Elution of bound proteins with 0.25 M α-D-methylmannopyranoside resulted in a broad major peak followed by a minor peak. There was heterogeneity in binding of gp75 antigen to the Con A column, indicated by multiple peaks of gp75 activity during elution. This was observed consistently over multiple column runs. It was observed that gp75 in melanocytes and melanoma cells exists as 2 mature forms that differ in either the number or the composition of Asn-linked complex carbohydrates. However, heterogeneity in binding to Con A did not result from detectable differences in Asn-linked high-mannose carbohydrates on gp75. This was shown by radioiodination of the eluted peak fractions, and immunoprecipitation of gp75 with MAb TA99 followed by removal of high mannose carbohydrate chains by endo-β-N-acetylglucosaminidase H (Endo H) digestion. All peaks tested contained 2 mature forms of gp75 which, after Endo H digestion, produced 63- and 66-kDa bands on SDS-PAGE.

Fractions from the Con A eluate containing gp75 were pooled and applied to MAb TA99 affinity column. There was complete depletion of gp75 in the effluent of the affinity column, as measured by ELISA, and by silver staining of SDS-PAGE. The effluent contained 92% of the total protein loaded on the column. Conditions for elution of bound gp75 were predetermined on the basis of inhibition of MAb TA99 binding to permeabilized and methanol:acetone-fixed SK-MEL-19 melanoma cells by ELISA (as described in "Material and Methods"). Binding of MAb TA99 to gp75 could be abrogated or reversed by 0.1 M glycine HCl buffer, pH 3.1. Elution of the column with 0.1 M glycine/HCl buffer yielded approximately 0.5 nmole of purified gp75 from 1.7 mg of protein loaded on the column, as determined by intensity of silver-stained gp75 band on polyacrylamide gel. Elution of gp75 from the TA99 antibody affinity column also resulted in leaching of trace amounts of TA99 antibody (heavy and light chains) which appeared as additional minor bands of 53, 28 and 26 kDa on silver-stained gel. It was confirmed that these additional bands originated from TA99 antibody bound to the column and not from the SK-MEL-19 antigen preparation by: (1) immunoprecipitation of the 53-, 28-, and 26-kDa proteins with rabbit anti-mouse IgG antibody, and (2) demonstration that these bands did not originate from a radioiodinated preparation of the SK-MEL-19 lysate. A summary of the purification of gp75 is shown in Table I.

TABLE I

PURIFICATION OF gp75

| Protein fraction | Total protein[1] (mg) | Units of gp75 activity[2] | Specific activity (units/mg) |
|---|---|---|---|
| Deoxycholate-solubilized membrane | 236 | 250 | 1.05 |
| Mono Q column bound | 6.27 | 128 | 20.41 |
| Con A-Sepharose bound | 1.73 | 118 | 68.20 |
| TA99 affinity column eluate | 0.035[3] | ND | — |

[1]Amount of protein in pooled, dialyzed fractions was measured by Bradford's dye binding method (1976). -
[2]One unit of activity was defined as the amount of protein required for half-maximal inhibition of MAb TA99 (300/mg) binding to SK-MEL-19 cells. -
[3]Amount of purified gp75 in the TA99 affinity column eluate was estimated by approximation of intensity of silver-stained band on SDS-PAGE. ND. not determined.

Affinity-purified gp75 was utilized for amino-acid analysis. Amino-acid composition of gp75 is shown in Table II.

TABLE II

AMINO ACID COMPOSITION OF gp75
Number of residues/molecule of gp75
(pmol)

| | | | |
|---|---|---|---|
| Asx | 63(970) | Tyr | 13(205) |
| Glx | 60(922) | Ser | 47(730) |
| Gly | 55(854) | His | 10(160) |
| Arg | 33(502) | Thr | 34(525) |
| Ala | 30(467) | Pro | 32(492) |
| Val | 33(515) | Met | 1(11) |
| Ile | 15(235) | Leu | 41(628) |
| Phe | 26(397) | Lys | 6(90) |
| Cys | ND | Trp | ND |

Amino acid analysis was performed on 2 samples (600 and 800 ng) of purified gp75 transferred to PVDF membrane. Numbers in parenthesis are pmol of each amino acid detected.
Asx = sum of aspartic acid and asparagine;
Glx = sum of glutamic acid and glutamine.
ND = not determined.

Amino acid analysis was performed on 2 samples (600 and 800 ng) of purified gp75 transferred to PVDF membrane. Numbers in parenthesis are pmol of each amino acid detected. Asx=sum of aspartic acid and asparagine; Glx=sum of glutamic acid and glutamine. ND=not determined.

Sequences of 3 internal peptides of gp75 and partial sequence of gp75 cDNA have been shown in experiment 1. The amino-acid composition of gp75 was similar to that of N. crassa (Lerch, K., Longoni, C. and Jordi, E., Primary structure of tyrosinase from Neurospora crassa, J. biol. Chem., 257 6408–6413, 1982) and mammalian tyrosinases, and of the mouse b gene product (Shibahara, S., Tomita, Y., Sakakura, T., Nager, C., Chaudhuri, B. and Muller, R., Cloning and expression of cDNA encoding mouse tyrosinase, Nucl. Acids Res., 14, 2413–2427, 1986; Bouchard, B., Fuller, B., Vijayasaradhi, S. and Houghton, A. N., Induction of pigmentation in mouse fibroblasts by expression of human tyrosine, J. exp. Med., 169, 2029–2042, 1989; Cohen, T., Muller, R. M., Tomita, Y. and Shibahara, S., Nucleotide sequence of the cDNA endocing human tyrosinase-related protein, Nucl. Acids Res., 18, 2807, 1990). Attempts to perform N-terminal sequence analysis of gp75 by the Edman degradation method were not successful due to the presence of a blocked N-terminus. The N-terminal serine residue of N. crassa tyrosinase is also blocked, in this case by an acetyl group (Lerch, K., Longoni, C. and Jordi, E., Primary structure of tyrosinase from Neurospora crassa, J. biol. Chem., 257, 6408–6413, 1982).

Both gp75 and tyrosinase are 75-kDa membrane glycoproteins localized to melanosomes, have similar amino-acid compositions, approximately 40% amino-acid sequence identify (See experiment 1; Cohen, T., Muller, R. M., Tomita, Y. and Shibahara, S., Nucleotide sequence of the cDNA endocing human tyrosinase-related protein, Nucl. Acids Res., 18, 2807, 1990), and 2 potential cooper-binding sites (required for the catalytic activity of tyrosinase). Some investigators have proposed that mouse gp75 has tyrosine hydroxylase activity, a characteristic of the tyrosinase molecule (Hearing, V. J. Jimenez, M., Analysis of mammalian pigmentation at the molecular level, Pigment Cell Res., 2, 75–85, 1989).

Tyrosine hydroxylase activity was measured in the supernatants and immunoprecipitates of SK-MEL-19 melanoma cell extracts following precipitation with MAb TA99. There was no specific depletion of enzyme activity by TA99; 94% of tyrosine hydroxylase activity could be recovered in the supernatant following incubation of cell extracts with either a control antibody (MAb F23) or MAb TA99 (Table III).

No significant decrease in the recovery of tyrosine hydroxylase activity in the supernatant was observed with increased antibody concentration up to 300 μg/ml. No enzyme activity was recovered in the immunoprecipitates. These results demonstrate that almost all tyrosine hydroxylase activity in human melanoma cells is accounted for by a molecule(s) that is distinct from the gp75 antigen.

TABLE III

TYROSINE HYDROXYLASE ACTIVITY FOLLOWING IMMUNOPRECIPITATION WITH MAb TA99

| | Antibody concentration | cpm $^3H_2O$ released per μg protein/hr (% total enzyme activity)[1] | |
|---|---|---|---|
| MAb | (μg/ml) | Supernatant | Pellet |
| Expt. A: | | | |
| Buffer[2] | — | 772(100%) | 170 |
| F23[3] | 60 | 727(94%) | 189 |
| TA99 | 60 | 735(95%) | 140 |
| Expt. B: | | | |
| Buffer | — | 550(100%) | 45 |
| TA99 | 60 | 537(97%) | 37 |
| | 300 | 530(96%) | 46 |

[1]Numbers in parenthesis are percentage of tyrosine hydroxylase activity recovered in supernatants compared to buffer control (= 100%). -
[2]Control tubes were incubated with PBS and then protein A Sepharose as described in "Material and Methods". -
[3]Mouse MAb F23 (IgG$_{2a}$) is an anti-colon carcinoma MAb that does not react with human melanocytic cells.

Tyrosine hydroxylase activity was also measured in fractions containing gp75 during purification. Total cellular tyrosine hydroxylase activity co-purified with gp75 during detergent solubilization of post-nuclear membranes, gradient elution of proteins bound to Mono Q anion exchange column, and Con A fractionation. This is consistent with the substantial homology between gp75 and human tyrosinase. However, gp75 and tyrosine hydroxylase activity were dissociated on MAb TA99 affinity column. When a deoxycholate-solubilized, Con A-purified fraction of SK-MEL-19 was applied to a MAb TA99 affinity column, ≧75% of tyrosine hydroxylase activity was recovered in the effluent while gp75 activity was completely depleted (Table IV).

TABLE IV

RECOVERY OF TYROSINE HYDROXYLASE ACTIVITY
DURING PURIFICATION OF gp75

| Fraction | Protein (μg) | Total tyrosine hydroxylase activity (units)[1] | Specific activity (units/mg) |
| --- | --- | --- | --- |
| Con A-Sepharose column bound | 160 | 34 | 215.68 |
| TA99 affinity column Flow-through | 120 | 25 | 210.13 |

[1]One unit of enzyme activity is the amount of protein required to release one micromole of $^3H_2O$ from $^3H$-tyrosine in 1 hr at 37° C.

Although eluted gp75 contained no tyrosine hydroxylase activity, it is possible that column eluting conditions abrogated enzyme activity. These results support the conclusion that most, if not all, tyrosine hydroxylase activity in melanocytic cells resides in a protein which is distinct from gp75.

The gp75 antigen is a membrane-bound glycoprotein that is expressed in pigmented human melanocytes and melanomas and is not detected in non-pigmented melanomas or in non-mefanocytic cell types (Thomson, T. M., Mattes, J. M., Roux, L., Old, L. J. and Lloyd, K. O., Pigmentation-associated glycoprotein of human melanoma and melanocytes: definition with a mouse monoclonal antibody, *J. invest. Dermat.*, 85, 169–174, 1985; Thomson, T. M., Real, F. X., Murakami, S., Cordon-Cardo, C., Old, L. J. and Houghton, A. N., Differentiation antigens of malanocytes and melanoma: analysis of melanosome and cell surface markers of human pigmented cells with monoclonal antibodies, *J. invest. Dermat.*, 90, 459–466, 1988). Immunoelectron microscopy studies have revealed that MAb TA99 binds at or near the melanosomal membrane (Thomson, T. M., Real, F. X., Murakami, S., Cordon-Cardo, C., Old, L. J. and Houghton, A. N., Differentiation antigens of malanocytes and melanoma: analysis of melanosome and cell surface markers of human pigmented cells with monoclonal antibodies, *J. invest. Dermat.*, 90, 459–466, 1988). The intracellular localization of gp75 in the melanoma cells appears to make gp75 inaccessible to the immune system. However, IgG antibodies against gp75 have been detected in a melanoma patient (Mattes, J. M., Thomson, T. M., Old, L. J. and Lloyd, K. O., A pigmentation-associated, differentiation antigen of human melanoma defined by a precipitating antibody in human serum, *Int. J. Cancer*, 32, 717–721, 1983). In this respect, MAb TA99 recognizes the same gp75 antigen precipitated by the IgG antibodies in the melanoma patient (Vijayasaradhi, S., Bouchard, B. B. and Houghton, A. N., The melanoma antigen gp75 is the human homologue of mouse b (brown) locus gene, *J. exp. Med.*, 171, 1375–1380, 1990). Radiolabelled MAb TA99 injected intravenously effectively localized to melanoma xenografts in athymic mice (Welt, S., Mattes, J. M., Grando, R., Thomson, T. M., Leonard, R. W., Zanzonico, P. B., Bigler, R. E., Yeh, S., Oettgen, H. F. and Old, L. J., Monoclonal antibody to an intracellular antigen images human melanoma transplants in nu/nu mice, *Proc. nat. Acad. Sci.* (Wash.), 84, 4200–4204, 1987), suggesting the gp75 antigen is available to the immune system.

The melanosomal glycoprotein tyrosinase is encoded by a gene that maps to the mouse c (albino) locus, while gp75 maps to the b (brown) locus. Tyrosine and gp75 have a number of shared properties. In addition to similar physical properties, as evident from co-purification of gp75 and tyrosinase activity through multiple chromatographic steps, these 2 proteins also share molecular identity (43.1% at amino acid and 55.3% nucleotide level) (Vijayasaradhi, S., Bouchard, B. B. and Houghton, A. N., The melanoma antigen gp75 is the human homologue of mouse b (brown) locus gene, *J. exp. Med.*, 171, 1375–1380, 1990; Cohen, T., Muller, R. M., Tomita, Y. and Shibahara, S., Nucleotide sequence of the cDNA endocing human tyrosinase-related protein, *Nucl. Acids Res.*, 18, 2807, 1990).

Anti-tyrosine antibodies cross-react with tyrosinase, the b (brown) locus protein and possibly a family of related proteins (Shibahara, S., Tomita, Y., Sakakura, T., Nager, C., Chaudhuri, B. and Muller, R., Cloning and expression of cDNA encoding mouse tyrosinase, *Nucl. Acids Res.*, 14, 2413–2427, 1986; Jackson, I. J., A cDNA encoding tyrosinase-related protein maps to the brown locus in mice, *Proc. nat. Acad. Sci.* (Wash.), 85, 4392–4396, 1988; Hearing, V. J., and Jimenez, M., Analysis of mammalian pigmentation at the molecular level, *Pigment Cell Res.*, 2, 75–85, 1989). Therefore, it was important to demonstrate that the purified gp75 antigen is distinct from tyrosinase. The gp75 and tyrosine hydroxylase activity co-purified, but most tyrosinase enzyme activity could be dissociated from gp75 during purification with TA99 affinity chromatography. Most total cellular tyrosine hydroxylase activity was recovered in the flow-through of a MAb TA99 affinity column, suggesting that tyrosine hydroxylase activity is catalyzed by a molecule that is distinct from gp75. Consistent with this observation is the fact that MAb TA99 does not immunoprecipitate or deplete tyrosine hydroxylase activity (Table IV; Thomson, T. M., Mattes, J. M., Roux, L., Old, L. J. and Lloyd, K. O., Pigmentation-associated glycoprotein of human melanoma and melanocytes: definition with a mouse monoclonal antibody, *J. invest. Dermat.*, 85, 169–174, 1985). Jimenez, M., Malvoy, L. and Hearing, V. J., Specific identification of an authentic clone for mammalian tyrosinase, *J. biol. Chem.*, 264, 3397–3403, 1989 have employed anti-peptide antibodies against the mouse b locus protein, and have suggested that the b protein accounts for 15–30% of tyrosinase activity in mouse melanoma cells. Our results suggest that gp75 contains no tyrosine hydroxylase activity. However, the possibility that gp75 has very weak tyrosine hydroxylase activity that accounts for 5% of the enzyme activity in pigmented melanoma cells can not be ruled out.

What is claimed is:

1. An isolated nucleic acid molecule which encodes gp75 comprising the sequence shown in FIG. 3.

2. An isolated cDNA molecule of the nucleic acid molecule of claim 1.

3. An expression vector comprising a DNA sequence essential for replication of the vector and the cDNA molecule of claim 2 adapted for expression in a host.

4. The expression vector of claim 3, whereby the expression vector is vaccinia virus.

5. A plasmid comprising the isolated nucleic acid molecule of claim 1.

6. A plasmid of claim 5, designated GP75 E1.

7. A bacterial cell containing the plasmid of claim 6 with ATCC Accession No. 68565.

8. An expression vector comprising a DNA sequence essential for replication of the vector and an isolated cDNA molecule of an isolated nucleic acid molecule whose sequence encodes the amino acid sequence for a fragment of gp75, where the isolated cDNA molecule has the sequence shown in FIG. 3 and is adapted for expression in a host.

* * * * *